(12) United States Patent
Reddy et al.

(10) Patent No.: US 9,175,300 B2
(45) Date of Patent: Nov. 3, 2015

(54) METHOD OF EXPRESSING FOREIGN PROTEIN IN PLASTIDS

(75) Inventors: Vanga Siva Reddy, New Delhi (IN);
Sadhu Leelavathi, New Delhi (IN);
Amit Bhardwaj, New Delhi (IN)

(73) Assignees: Vanga Siva Reddy, New Delhi (IN);
Sadhu Leelavathi, New Delhi (IN);
Amit Bhardwaj, New Delhi (IN)

( * ) Notice: Subject to any disclaimer, the term of this patent is extended or adjusted under 35 U.S.C. 154(b) by 978 days.

(21) Appl. No.: 13/147,004

(22) PCT Filed: Nov. 27, 2009

(86) PCT No.: PCT/IN2009/000685
§ 371 (c)(1),
(2), (4) Date: Jul. 29, 2011

(87) PCT Pub. No.: WO2010/061404
PCT Pub. Date: Jun. 3, 2010

(65) Prior Publication Data
US 2012/0058512 A1    Mar. 8, 2012

(30) Foreign Application Priority Data
Nov. 27, 2008    (IN) .......................... 2689/DEL/2008

(51) Int. Cl.
*C12N 15/62*    (2006.01)
*C07K 14/195*    (2006.01)
*C12N 15/82*    (2006.01)
*C12N 9/42*    (2006.01)

(52) U.S. Cl.
CPC .......... *C12N 15/8214* (2013.01); *C12N 9/2434* (2013.01); *C12N 15/625* (2013.01)

(58) Field of Classification Search
None
See application file for complete search history.

(56) References Cited

U.S. PATENT DOCUMENTS

2004/0078848 A1    4/2004    Lebel et al.
2008/0274143 A1*   11/2008   Daniell .................... 424/228.1

FOREIGN PATENT DOCUMENTS

WO    00/20612 A2    4/2000
WO    03/012094 A1   2/2003

OTHER PUBLICATIONS

Bally et al (Plant Biotechnology Journal, 6, pp. 46-61, 2008).*
Leelavathi et al (Molecular Breeding, 11, pp. 59-67, 2003).*
International Preliminary Report on Patentability dated May 31, 2011 for Application No. PCT/IN2009/000685.
Database EMBL Apr. 15, 2005, XP002571875 Database accession No. AF015445.
Boehm Robert et al: "Active expression of the ubiA gene from *E. coli* in tobacco: Influence of plant ER-specific signal peptides on the expression of a membrane-bound prenyltransferase in plant cells" Transgenic Research, vol. 9, No. 6, Dec. 2000, pp. 477-486, XP002571876 ISSN: 0962-8819.

* cited by examiner

*Primary Examiner* — David T Fox
*Assistant Examiner* — Stephen Uyeno
(74) *Attorney, Agent, or Firm* — Ladas & Parry LLP

(57) ABSTRACT

The present invention relates to a method of expressing a foreign protein in the plastid of a host cell and secreting said protein into the cytoplasm of the host cell comprising the steps of making a construct of vector linked to a coding sequence of the fusion protein comprising of signal peptide sequence followed by in-frame fusion to a foreign gene; and stably integrating said construct into the plastid genome. The present invention also relates to a method of targeting the expressed and secreted proteins from the plastids to the nucleus of the host cell. The present invention further relates to the method where the host cell is of any higher plant or any organism including single cell algae.

Figure 1:
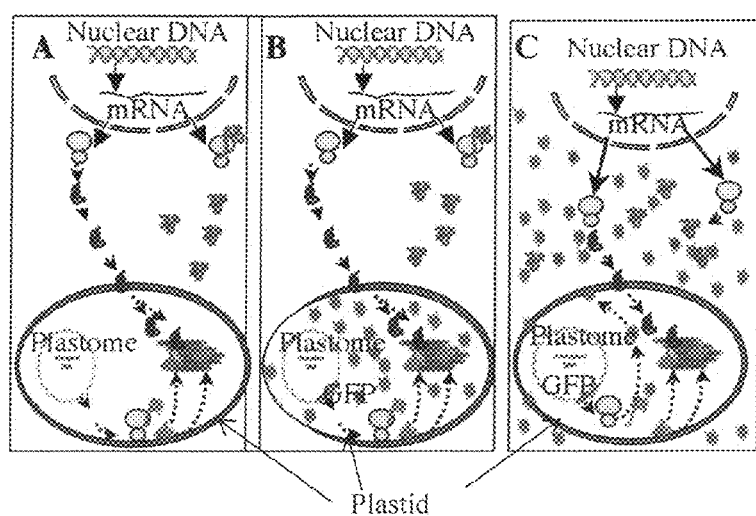

9 Claims, 6 Drawing Sheets
(6 of 6 Drawing Sheet(s) Filed in Color)

Figure 5. Expression of SP-NLS-GFP in tobacco chloroplasts: A. Partial map of construct used used in the study. B-C. Cellular localization of SP-NLS-GFP expressed in tobacco chloroplasts. The SP-NLS-GFP expressed in the chloroplasts is expected to secrete into cytoplasm due to the presence of SP and the NLS is expected to target the GFP further into the nucleus. Green fluorescence can be seen mostly localized in the nucleus, providing direct evidence for the presence of a fully functional secretary pathway again in tobacco chloroplasts and the ability of NLS from SV-40 antigen to target the GFP into the nucleus. B, C and D., respectively. Protoplasts from the plant leaves transformed with the above construct seen in phase contrast (A), DAPI stained nuclei (C) and GFP fluorescence (D). E, F and G. Enlarged view of select cells, from B, C, and D, respectively.

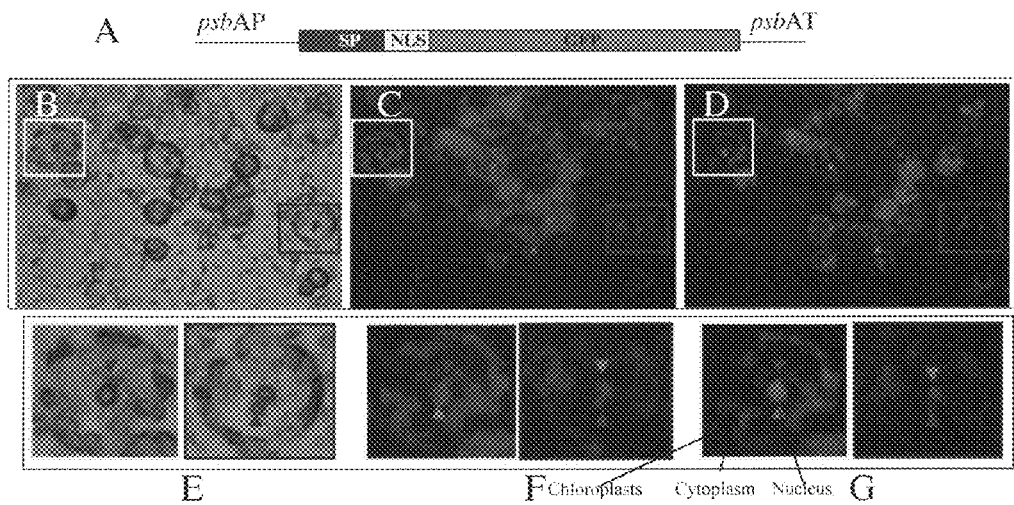

Figure 6. Hygromycin phosphotransferase (HPT) as a selectable marker for plastid transformation. Transplastomic tobacco plants developing under hygromycin selection 25 mg/L. (A-D). E. Partial map of construct pVSRSPHPT used in the plastid transformation. The SPHPT DNA was cloned into pVSR326 at BamHI and XhoI using the same enzymes
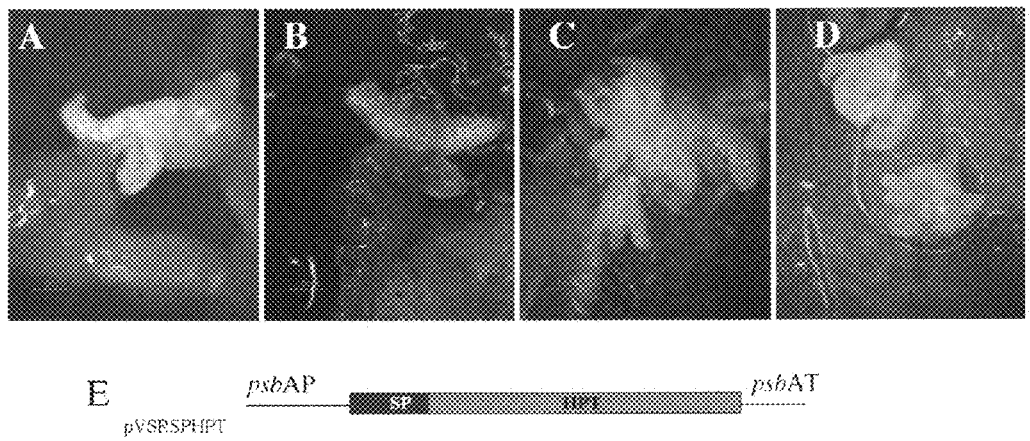

METHOD OF EXPRESSING FOREIGN PROTEIN IN PLASTIDS

FIELD OF THE INVENTION

The present invention relates to a method of expressing foreign protein in the plastid of a host cell and secreting said protein into the cytoplasm of a host cell. The present invention also relates to the targeting of the foreign protein in the nucleus of the host cell. The present invention further discloses that the method can be used in any host cell from any higher plant or any organism including single cell algae. The method can be used to target any protein from the plastids to any other organelle of the cell.

BACKGROUND OF THE INVENTION

Life on earth is largely supported by the solar energy captured by the green plastids (chloroplasts) present in land plants and green algae. Chloroplasts are considered to have originated from a photosynthetic prokaryote (a cyanobacterium) that entered into an endosymbiotic relationship with an early eukaryotic progenitor over a billion years ago [Goksoyr J, Nature 214; 1161, 1967; Martin and Müller, Nature 392; 37-41, 1998; Martin and Kowallik, Eur. J. Phycol. 34, 287-295, 1999]. During the course of evolution, majority of the chloroplast genome (plastome) has moved to the nucleus, leaving behind a small but functional genome in the chloroplasts coding key components involved in photosynthesis, transcription and translation machinery. Evolutionary analysis of Arabidopsis, cyanobacterial, and chloroplast genomes suggested that about 4,500 Arobidopsis nuclear-encoded proteins (~18% of the total nuclear-coding genes) might have been acquired from the cyanobacterial ancestor of the plastids [Martin W, Proc. Natl. Acad. Sci. USA 99, 12246-12251, 2002].

Such a large scale migration of organellar genome to the nucleus has necessitated the development of an elaborate protein import mechanism(s) from the cytosol into chloroplasts for their ultimate function by crossing the double membrane envelope that surrounds each plastid. The nuclear-encoded proteins destined to plastids are made as preproteins having usually a cleavable N-terminal amino acid extension (transit peptide) that target the protein into plastids via the general protein import pathway. The general protein import machinery of the plastids consists of protein complexes present in the outer (Toc) and inner (Tic) membranes of chloroplasts [Robson and Collinson, EMBO Reports 7, 1099-1103, 2006].

A comparative molecular structure and functional analysis indicated a high degree of similarity between the subunits present in the Toc and Tic complexes and with the prokaryotic protein secretion pathway SecYEG complexes. Indeed the complete genome sequence of Arabidopsis and rice revealed the presence of all the genes coding for the key components of SecYEG pathway involved in protein translocation in bacteria: SecA, SecY and SecE. Also genes coding for SecA and SecB known to be involved in the secretion of proteins through SecYEG pathway in bacteria are present in the nuclear genomes of land plants. Based on the genetic evidences and the similarity of the proteins at the molecular level, it has been postulated that the same protein export mechanism that functioned originally to secrete the proteins in bacteria might have now been operating in the opposite direction to import proteins from the host cell into the chloroplasts to cross the double membrane chloroplast envelop after suitable modification(s) during the course of evolution [McFadden, Curr. Opinion in Plant Biol. 2, 513-519, 1999].

In the present day, land plant plastids, it is not known whether the protein export mechanisms that were originally operating before the endosybiosis are still functional and a foreign protein expressed in chloroplasts can be secreted into the cytoplasm of plant. Therefore, one of our main goals is to understand the protein trafficking from chloroplasts into the cytoplasm and find out the transport mechanisms present in the chloroplasts that can export foreign proteins synthesized in the plastids into cytoplasm of the cell. Such an understanding not only throw light on the evolutionary changes that took place in the basic biological process in the eukaryotic cell over millions of years, but also provide opportunities to engineer plastid genome to express foreign proteins with functions outside the chloroplasts that include creation of post translational modifications such as glycosilation, a major limiting step in chloroplast genetic engineering but very important in biotechnological application. In addition, the implications of these findings in relation to the biosafety of genetically modified organisms (GMOs) in the context of environment and biodiversity are discussed.

Chloroplasts are generally believed to have originated from a photosynthetic cyanobacterium-like prokaryote. During the course of evolution spanning over a billion years the prokaryotic organism has entered into an endosymbiontic relationship with the early eukaryotic cell. As a consequence majority of the chloroplast genome has moved to the nuclear genome and the corresponding proteins synthesized in the cytoplasm are imported back into plastids crossing the double membrane envelop through protein import mechanisms. It is not known whether the original protein export mechanisms that were operating before the endosymbiosis are still functional in the present day chloroplasts or not. The present invention, for the first time, the presence of evolutionarily conserved and fully functional prokaryotic-type protein secretary pathway in chloroplasts of higher plants, operating just in opposite direction to the well established general protein import pathway. The implications of the newly discovered functionally usable prokaryotic-type secretary pathway in chloroplasts in the evolution of eukaryotic cell, for biotechnological applications and in the biosafety of transgenics in the context of environment and biodiversity are discussed.

Biosafety is a serious public concern today due to large scale deployment of GMOs into the environment in several countries across the globe and this is another important area where the present invention is expected to have a major impact. As plastids are inherited maternally in most crops, chloroplast genetic engineering is considered as a better strategy to contain foreign gene flow to untransformed plants and wild relatives [Daniell H, Nature Biotechnology 20, 581-586, 2002; Ruf et. al., Proc. Natl. Acad. Sci. USA 104, 6998-7002, 2007; Savb and Maliga, Proc. Natl. Acad. Sci. USA 104, 7003-7008, 2007], a perceived threat to ecological imbalance and a major challenge for the conservation of biodiversity. The application of the chloroplast genetic engineering in plant biotechnology is limited so far to only those few genes that have or can function from within the chloroplasts [Maliga P, TRENDS in Biotechnology 21, 20-28, 2003; Daniell et. al., TRENDS in Plant Sci. 6, 219-226, 2001].

The present invention discloses that any foreign protein having function(s) out side the chloroplast can now be expressed in chloroplasts and target the protein to its site of function. With the use of appropriate targeting peptides it is possible in future to target the chloroplast expressed recombinant proteins in to any sub-cellular compartment in the cell. This would essentially allow one to contain the transgene flow by integrating the foreign gene into plastid genome that would improve the biosafety of the GMO's to the environment to a very high level and at the same time use the gene function(s) in any compartment of the cell.

OBJECTS OF THE INVENTION

It is an important object of the present invention to provide a method of expressing foreign protein in the plastid of a host cell and secreting said protein into the cytoplasm of the host cell comprising the steps of making a construct of vector linked to a coding sequence of the fusion protein comprising of signal peptide sequence followed by in-frame fusion to a foreign gene and stably integrating said construct into the plastid genome.

Another object of the present invention is to provide a method of expressing foreign protein in the plastid of a host cell, secreting said protein into the cytoplasm of the host cell and targeting said protein to the nucleus of the host cell comprising the steps of making a construct of vector linked to a coding sequence of the fusion protein comprising of a signal peptide sequence followed by in-frame fusion to a nuclear localization signal followed by foreign gene and stably integrating said construct into the plastid genome.

Yet another object of the present invention is to provide a method where the signal peptide is the signal peptide of xylanase enzyme or any prokaryotic signal peptide having similar function.

Still another object of the present invention is to provide a method where the foreign protein is Green Fluorescent Protein or any other protein.

Yet another object of the present invention is to provide a method where the host cell is of any higher plant or any organism including single cell algae.

SUMMARY OF THE INVENTION

The above and other objects of the present invention are achieved by a method of expressing foreign protein in the plastid of a host cell and secreting said protein into the cytoplasm of the host cell comprising the steps of making a construct of vector linked to a coding sequence of the fusion protein comprising of signal peptide sequence followed by in-frame fusion to a foreign gene and stably integrating said construct into the plastid genome.

In another embodiment of the present invention, a method of expressing foreign protein in the plastid of a host cell, secreting said protein into the cytoplasm of the host cell and targeting said protein to the nucleus of the host cell comprising the steps of making a construct of vector linked to a coding sequence of the fusion protein comprising of a signal peptide sequence followed by in-frame fusion to a nuclear localization signal followed by foreign gene stably integrating said construct into the plastid genome is disclosed.

Preferably, said signal peptide has the amino acid sequence having SEQ ID NO. 1 encoded by a DNA sequence having SEQ ID NO. 2.

Preferably, said signal peptide comprises of N-terminal protein of 55 amino acid of xylanase enzyme.

Preferably, said signal peptide is substituted with any prokaryotic signal peptide having similar function.

Preferably, said foreign protein has amino acid sequence SEQ ID NO. 3 encoded by a DNA sequence having SEQ ID NO.4.

Preferably, said foreign protein is Green Fluorescent Protein.

Preferably, said foreign protein is substituted with any protein having similar function.

Preferably, said nuclear localization signal has amino acid sequence having SEQ ID NO.5 encoded by a DNA sequence having SEQ ID NO.6.

Preferably, said nuclear localization signal is obtained from SV 40 antigen.

Preferably, said host cell is of tobacco plant.

Preferably, said host cell is of any higher plant including angiosperms or any organism including single cell algae like chlorella, chlamydomonas, etc.

Preferably, said vector is a plasmid pVSR 326.

In another embodiment of the present invention, A method of expressing a foreign protein in the plastid of a host cell selected from the group comprising of any higher plant or any organism including single cell algae; and secreting said protein into the cytoplasm of the host cell comprising the steps of making a construct of pVSR 326 plasmid vector linked to a coding sequence of the fusion protein comprising of signal peptide sequence selected from the group comprising of signal peptide of xylanase or any prokaryotic signal peptide having similar function, followed by in-frame fusion to a foreign gene, selected from group comprising of Green Fluorescent Protein or any other protein; and stably integrating said construct into the plastid genome is disclosed.

In yet another embodiment of the present invention, a method of expressing a foreign protein in the plastid of a host cell selected from the group comprising of any higher plant or any organism including single cell algae; secreting said protein into the cytoplasm of the host cell and targeting said protein to the nucleus of the host cell comprising the steps of making a construct of pVSR 326 plasmid vector linked to a coding sequence of the fusion protein comprising of signal peptide sequence selected from the group comprising of signal peptide of xylanase or any prokaryotic signal peptide having similar function, followed by in-frame fusion to a nuclear localization signal from SV 40 antigen, followed by a foreign gene selected from group comprising of Green Fluorescent Protein or any other protein; and stably integrating said construct into the plastid genome is disclosed.

In still another embodiment of the present invention, a method for exporting proteins from plastids to other cell organelles like mitochondria, endoplasmic reticulum, golgi apparatus, etc. is disclosed.

In yet another embodiment, a method for achieving post translational modifications such as glycosylation is disclosed.

In still another embodiment of the present invention, a method is used to improve the biosafety of genetically modified organisms (GMOs) is disclosed.

BRIEF DESCRIPTION OF ACCOMPANYING DRAWINGS

The file of this patent contains at least one drawing or photograph executed in color. Copies of this patent with color drawing(s) or photograph(s) will be provided by the Patent and Trademark Office upon request and payment of necessary fee.

FIG. 1: Schematic diagram showing the gene expression, protein trafficking and localization in the plant cell. A. Proteins coded by the nuclear genome enter into chloroplasts through protein import mechanism facilitated by specific targeting signal peptides. B. Integration of GFP gene into chloroplast genome under chloroplast specific promoter is expected to lead in the expression and accumulation of the GFP protein inside the chloroplasts only and not in the cytoplasm. C. The SP-GFP fusion protein expressed in the chloroplasts is expected to secrete into cytoplasm due to the presence of bacterial SP if the secretary pathway of cyanobacterial origin is still present in a functional state.

Figure 2:
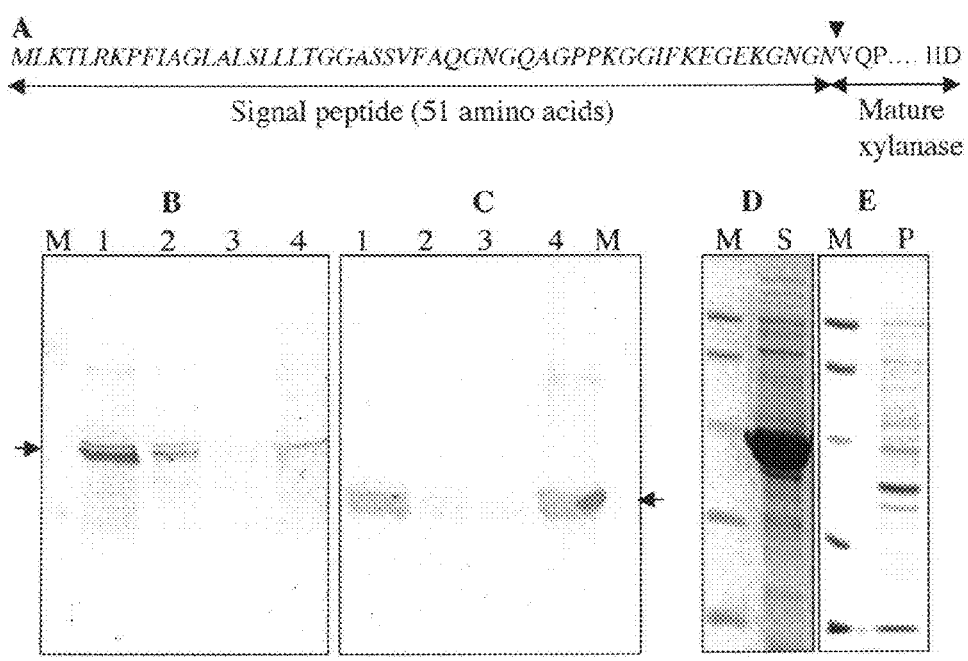

FIG. 2: Secretary signal peptide of xylanase from *B. subtilis* and the secretion of the enzyme in *E. coli*. A. The N-terminal 55 amino acids (SP) get cleaved from the mature xylanase upon the secretion of the enzyme in *B. subtilis*. B-C. M. Marker 1. Media supernatant 2. Periplasm 3. Cytosol 4. Membrane fraction S. Soluble fraction P. pellet. The 55 amino acid signal peptide is found to be necessary and just sufficient to direct the export of xylanase in *E. coli* (Fig. B) as well as GFP when expressed in *E. coli* (Fig. C). D-E. Xylanase when expressed in a in *E. coli* without first 55 amino acids signal peptide remained in side the bacterial cell, in a soluble form.

Figure 3:
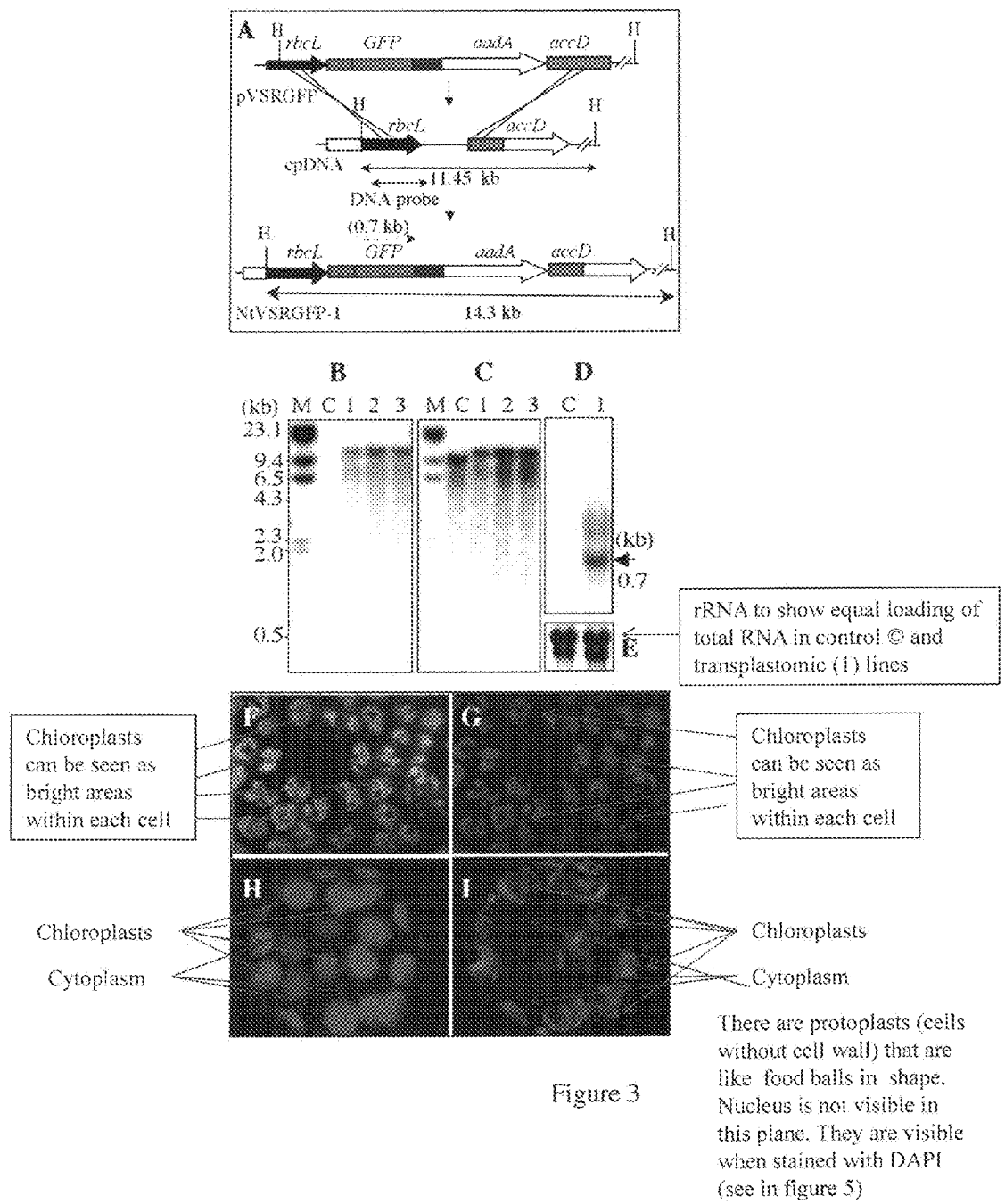

FIG. 3: Physical map of the transplastomic chloroplast genome. Molecular analysis and confocal microscope is used to follow the expression and the localization of the GFP in the cells. Southern hybridization provides a clear evidence for the stable and site specific integration of the GFP into tobacco plastid genome (FIG. 3A-C). GFP is expected to get integrated into plastid genome site specifically at the intergenic spacer region between rbcL and accD genes through two homologous recombinations (FIG. 3A). Northern blot analysis confirms efficient transcription of GFP under psbA promoter. An expected size transcript (0.7 kb) is observed in the transformed tobacco plant and no such signal is present in the control untransformed plant (FIG. 3D). The rRNA is used as a loading control (FIG. 3E). When observed under confocal microscope, the GFP is found to be localized only in the chloroplasts when expressed without signal peptide (FIG. 3F-I).

Figure 4:
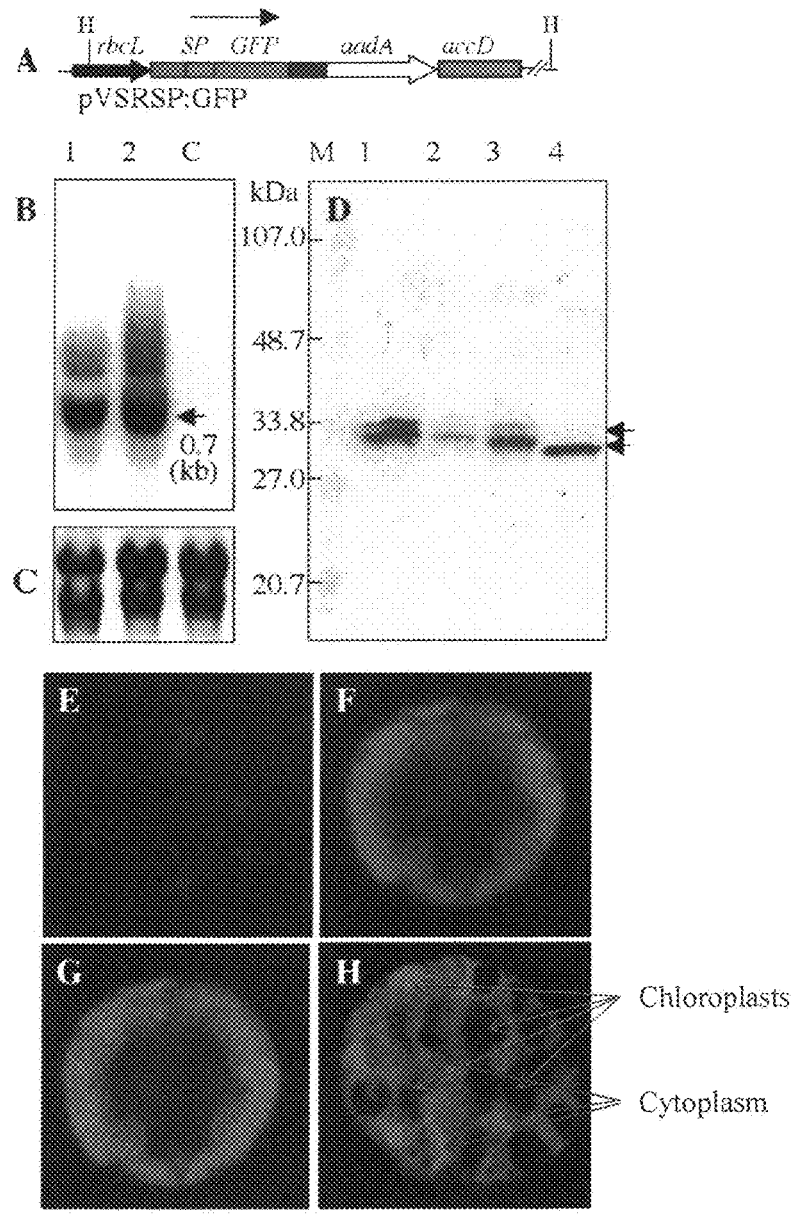

FIG. 4: Expression and localization of SP-GFP. A. Physical map of SP-GFP construct. B-C. Northern blot analysis confirms the expression of the SP:GFP fusion gene in the transgenic plants. C. Western blot analysis is used to check the processing of the SP:GFP fusion protein. Two bands, one corresponding to the full length of SPrGFP fusion protein and the second corresponding to the processed GFP are observed. A close observation of the two bands indicate that lower bad corresponding to the processed GFP is more prominent, suggesting that the bacterial signal peptide get processed very efficiently in the chloroplast membranes. D. Protein extracts from the plants expressing GFP alone is used as a control for the comparison of the protein sizes. E-H. Confocal images clearly provide the evidence for the presence of the GFP inside the chloroplasts as well as in the cytoplasm. The GFP fluorescence is stronger in the cytoplasm indicating the efficient transport of the chloroplast expressed recombinant GFP protein.

FIG. 5: Expression of SP-NLS-GFP in tobacco chloroplasts: A. Partial map of construct used in the study. Protoplasts from the plant leaves transformed with the above construct seen in B. phase contrast, C. DAPI stained nuclei and D. GFP fluorescence. E,F,G. Enlarged view of select cells, from B, C, and D, respectively.

FIG. 6: Hygromycin phosphotransferase (HPT) as a selectable marker for plastid transformation. A-D. Transplastomic tobacco plants developing under hygromycin selection 25 mg/L E. Partial map of construct pVSRSPHPT used in the plastid transformation.

DETAILED DESCRIPTION OF THE INVENTION

The present invention discloses a method of expressing a foreign protein in the plastid of a host cell and secreting said protein into the cytoplasm of a host cell. The present invention also discloses targeting of the foreign protein in the nucleus of the host cell. The present invention discloses that the methods can be used in any host cell from any higher plant or any organism including single cell algae and to target any protein from the plastids to any other organelle of the cell.

Xylanase is produced as a pre-protein with a cleavable 55 amino acids from the N-terminal end that target the enzyme to membrane for the secretion into out side environment. The 55 amino acid signal peptide is found to be necessary and just sufficient to direct the export of xylanase in *E. coli* as well as GFP when expressed in *E. coli* and therefore, used as a model bacterial-targeting signal peptide to test the presence of any secretary system in chloroplasts, reminiscence of prokaryotic secretary system. Xylanase when expressed in a in *E. coli* without first 55 amino acids signal peptide remained in side the bacterial cell, in a soluble form.

The tobacco chloroplast genome is stably transformed to express a Green Fluorescent Protein (GFP) with or without a bacterial signal peptide (SP) from xylanase enzyme fused at the N-terminal end. The GFP is expected to be localized within the chloroplasts when expressed alone. On the other hand, SP:GFP fusion protein is expected to be secreted into the cytoplasm if the plastids retained the prokaryotic protein secretary mechanism. Molecular analysis and confocal microscope is used to follow the expression and the localization of the GFP in the cells. Southern hybridization provided a clear evidence for the stable and site specific integration of the GFP into tobacco plastid genome. GFP is expected to get integrated into plastid genome site specifically at the intergenic spacer region between rbcL and accD genes through two homologous recombinations. Northern blot analysis confirmed efficient transcription of GFP under psbA promoter.

Molecular analysis of the transgenic plants transformed with pVSRSP:GFP confirms the stable and site specific integration of the SP:GFP into the chloroplast genome of the tobacco plants. Northern blot analysis confirms the expression of the SP:GFP fusion gene in the transgenic plants. The first 55 amino acids signal peptide is expected to be cleaved in the chloroplast membrane if the SP:GFP is targeted to the membrane for the secretion into cytoplasm. Western blot analysis is used to check the processing of the SP:GFP fusion protein. Confocal images clearly provide the evidence for the presence of the GFP inside the chloroplasts as well as in the cytoplasm. The confocal imaging results are further supported the results observed in the Western blot analysis.

The present invention, for the first time, provides a direct evidence to show the presence of a functionally operating and evolutionarily conserved prokaryotic protein secretary pathway in the chloroplasts of higher plants similar to the one present in bacteria, the progenitor of the plastids which is operating just in the opposite direction to the conventionally evolved general protein import pathway in chloroplasts. Further, the present invention discloses that any proteins synthesized in the chloroplasts are secreted into the cytoplasm and/or targeted to the nucleus. The ability to secrete chloroplast-expressed proteins into cytoplasm demonstrated in the present invention not only widen the scope to express proteins with functions outside the chloroplasts but also provides a new opportunity to obtain desired post translational modification(s) necessary for several recombinant proteins intended to be produced through plant based molecular farming for therapeutic purposes, currently a major limitation for chloroplast expressed proteins.

The present invention further teaches that the GFP secreted from the chloroplasts into cytoplasm can be targeted further into the nucleus as this provides evidence to the fact that the exported protein from the chloroplasts into the cytoplasm or any other sub-cellular compartments are biologically active.

To provide evidence for the targeting of chloroplast expressed proteins into the nucleus, a construct is made where a nuclear localization signal from SV40 antigen is fused in frame between the SP and GFP. In this case the GFP is expected to get targeted itself further into the nucleus after it is exported into the cytoplasm from the chloroplasts due the presence of NLS signal sequence at the N-terminal end of the target protein. The SP-NLS-GFP gene cassette is integrated into the chloroplast genome of tobacco, following the procedures essentially similar to SP-GFP construct. The present invention for the first time provides a direct molecular evidence to establish a fact that a functional protein export pathway is present in the present day land plans, similar to the one present in prokaryotes like bacteria, the progenitor of the plastids and the exported proteins can be modified further to target to other sub-cellular compartments. The use of Hygromycin phosphotransferase (HPT) as a selectable marker for plastid transformation is tested.

The present invention is illustrated and supported by the following examples. These are merely representative examples and optimization details and are not intended to restrict the scope of the present invention in any way.

Example—I

Gene Expression, Protein Trafficking and Localization in the Plant Cell

Proteins coded by the nuclear genome enter into chloroplasts through protein import mechanism facilitated by specific targeting signal peptides (FIG. 1A). In order to test the presence of a functional prokaryotic-type protein secretary system similar to the one present in the bacterial systems in the plastids of higher plants, the present invention stably transforms tobacco chloroplast genome as described earlier using particle bombardment [Reddy et. al., *Mol. Breed.* 9, 259-269, 2002] to express a Green Fluorescent Protein (GFP) [Hein et. al., *Nature* 373, 663-664, 1995] with or without a bacterial signal peptide (SP) from xylanase enzyme fused at the N-terminal end. This signal peptide has an amino acid sequence having SEQ ID NO. 1 (MLKTLRKPFIAGLA-LSLLLTGGASSVFAQGNGQAGPPKG-GIFKEGEKGNGNVQPF). This protein is encoded by a DNA sequence having SEQ ID NO. 2 ((ATGCTAAAAACGTTAAGAAAACCCTTCAT-TGCAGGACTAGCTTTATCATTATT ACTCACTGGTG-GAGCGAGCAGTGTATTTGCTCAAGGAAACGGT CAAGCTGGCC CACCAAAGGGAGGCATTTTTAAA-GAAGGAGAAAAAGGAAATGGCAATGTCC AAC-CTTTT). The GFP is expected to be localized within the chloroplasts when expressed alone (FIG. 1B). On the other hand, SP:GFP fusion protein is expected to be secreted into the cytoplasm if the plastids retained the prokaryotic protein secretary mechanism (FIG. 1C).

Example—2

Secretary Signal Peptide of Xylanase from *B. subtilis* and the Secretion of the Enzyme in *E. coli*

Xylanase (EC 3.2.1.8), a plant cell wall degrading enzyme from *Bacillus subtilis* [Gupta et. al., *Appl. Environ. Microbiol.* 66, 2631-2635, 2000; Manikandan K, *Pro. Sci.* 15, 1951-1960, 2006] is produced as a preprotein with a cleavable 55 amino acids from the N-terminal end (SP) that target the enzyme to membrane for the secretion into out side environment (FIG. 2A). When the recombinant xylanase is expressed along with the signal peptide, majority of the xylanase is present in the media supernatant followed by periplasmic space and membrane fraction. Cytoplasm has the lowest amount, indicating that the SP is able to target the xylanase efficiently to the membrane and secrete into the medium (FIG. 2B).

The Green Fluorescent protein has a protein sequence SEQ ID NO. 3 (MASKGEELFTGVVPILVELDGD-VNGYKFSVSGEGEGDATYGKLTLKFICTTGKLPV WPTLVTTFSYGVQCFSRYPDHMKRHD-FFKSAMPEGYVQERTIFFKDDGNYKTRAEV KFEGDTLVNRIELKGIDFKEDGNILGHK-LEYNYNSHNVYIMADKQKNGIKANFK HNIEDG-GVQLADHYQQNTPIGDGPVLLPDNHYL-STQSALSKDPNEKRDHMVLLEF VTAAGITHGMDELYKHDEL). This protein is encoded by a DNA sequence having SEQ ID NO. 4 (ATGGCAAG-TAAAGGAGAAGAACTTTTCACTGGAGT-TGTCCCAATTCTTGTTGA ATTAGATGGTGATGT-TAATGGGTACAAATTTTCTGTCAGTGGAGAGGGT GAAG GTGATGCAACATACGGAAAACTTACCCT-TAAATTTATTTGCACTACTGGAAAA CTACCTGTTC-CTTGGCCAACACTTGTCAC-TACTTTCTCTTATGGTGTTCAATGCT TTTCAAGATACCCAGATCATATGAAGCG-GCACGACTTCTTCAAGAGCGCCATG CCTGAGG-GATACGTGCAGGAGAGGACCATCTTCT-TCAAGGACGACGGGAACT ACAAGACACGTGCTGAAGT-CAAGTTTGAGGGAGACACCCTCGTCAACAGGAT CGAGCTTAAGGGAATCGATTTCAAGGAG-GACGGAAACATCCTCGGCCACAAG TTGGAATA-CAACTACAACTCCCACAACGTATACAT-CATGGCCGACAAGCAAA AGAACGGCATCAAAGCCAACTTCAAGAC-CCGCCACAACATCGAAGACGGCG GCGTG-CAACTCGCTGATCATTATCAA-CAAAATACTCCAATTGGCGATGGCCCT GTCCTTTTACCAGACAACCATTACCT-GTCCACACAATCTGCCCTTTCGAAAGAT CCCAAC-GAAAAGAGAGACCACATGGTCCTTCT-TGAGTTTGTAACAGCTGCTGG GATTACACATGGCATGGATGAACTATA-CAAACACGACGAACTCTAA).

When the SP is N-terminally fused in frame to GFP, a more or less similar process is observed except that the membrane fraction also has high amount of GFP (FIG. 2C). The 55 amino acid signal peptide is found to be necessary and just sufficient to direct the export of xylanase in *E. coli* and therefore, used as a model bacterial-targeting signal peptide to test the presence of any secretary system in chloroplasts, reminiscence of prokaryotic secretary system. When the recombinant xylanase is expressed without the signal peptide in *E. coli*, the majority of the enzyme is found in the cytoplasm in a soluble form (FIG. 2D). Pellet fraction has no detectable amount of enzyme (FIG. 2E).

Example—3

Molecular Analysis and Confocal Microscopy

The GFP is placed under a chloroplast specific promoter (psbA) and integrated into plastid genome using Particle Delivery System (PDS 1000, Biorad). The GFP and aadA transgenes are integrated into the intergenic spacer region between rbcL and accD genes. The aadA gene conferring resistance to spectinomycin is used as a selectable marker.

Two possible homologus recombinations that can lead to site specific integration of transgenes are shown by crossed lines. The Hind III restriction sites used for RFLP analysis is indicated along with the expected size of fragments (FIG. 3A).

Site-specific integration of the GFP is confirmed though Southern hybridization. Genomic DNA isolated from NtVS-RGFP1 (lane 1&2) and NtSP-GFP1 (lane 3) are digested with HindiIII, separated on agarose gel, blotted onto a nylon membrane Hybond N+. Blot and probed with GFP (B) and partial rbcL (C) gene probes (FIGS. 3B & C). Efficient transcription of GFP is confirmed using Northern blot analysis. An expected size of 0.7 kb transcript is found in the transplastomic plants (lane 1). No signal is found in the untransformed control plant (lane C) (FIG. 3D).

Ribosomal RNA shows equal loading of RNA in the blot (FIG. 3E). Localization of GFP is shown when the gene is integrated into tobacco chloroplast genome. Accumulation of GFP is limited to chloroplasts. Leaf tissue is treated with cellulase and macerozyme to release the protoplasts and the cells are observed under confocal microscope. Confocal imaging is carried out using AXIOObserverZ1 motorized inverted microscope with spectral confocal system model LSM510META (Zeiss) using objective 63× oil immersion (NA1,4). Images are acquired using blue diode lazar (ex 405 nm) and signals are collected at Emission range of 470 nm to 550 nm for GFP and autofluresecnce, respectively. Images are merged using LSM confocal software. Protoplasts when observed under visible light (FIG. 3F) and blue diode lazar (FIG. 3G). Confocal microscopy images of a single cell with chlorophyll fluorescence (red), indicative for chloroplasts (FIG. 3H) and for GFP (FIG. 3I), indicative for the presence of the GFP protein (green) are shown. The green GFP fluorescence is localized only in the chloroplasts of the transplastomic plant (NtVSRGFP1).

Example—4

Expression and Localization of SP-GFP

SP-GFP is placed under the same psbA expression signals that are use for the expression of GFP (FIG. 4A). Northern blot analysis shows efficient transcription of SP-GFP in Nt VSRSPGFP1 plants under psbA promoter (lane 1 & 2) (FIG. 4B). Western blot analysis is done to check the processing of bacterial signal peptide by the chloroplasts for the secretion of GFP (FIG. 4C). GFP antibodies have picked up two bands in all three independent transplastomic lines tested (lanes 1-3): one corresponding to the GFP (lower band) and the other to the unprocessed SP-GFP (upper band).

For a better comparison, the protein extract from the transplastomic line (NtVSRGFP1) expressing GFP alone is used (lane 4) (FIG. 4D). Confocal microscopy images of a single cell with GFP (FIG. 4E)) and chlorophyll (FIG. 4F) fluorescence are shown. Merged images of GFP and Chlorophyll fluorescence (FIG. 4G) and confocal image of a single protoplast from another transplastomic plant (FIG. 4H) are shown. The presence of prominent green fluorescence out side the chloroplasts, more prominently in the cytoplasm, in contrast to GFP localized within the chloroplasts when expressed without bacterial signal peptide.

Example—5

Targeting of Proteins in Nucleus

The present invention further discloses that if the GFP secreted from the chloroplasts into cytoplasm can be targeted further into the nucleus as this would provide evidence to the fact that the exported protein from the chloroplasts into the cytoplasm or any other sub-cellular compartments are biologically active.

To provide evidence for the targeting of chloroplast expressed proteins into the nucleus, a construct is made where a nuclear localization signal (NLS) from SV40 antigen [Daniell H, *Nature Biotechnology* 20, 581-586, 2002] is fused in frame between the SP and GFP (FIG. 5A). This nuclear localization signal has a protein sequence having SEQ ID NO. 5 (EFLEPPKKKRKVE). This protein sequence is encoded by a DNA sequence having SEQ ID NO. 6 (GAAT-TCCTCGAGCCTCCAAAAAAGAA-GAGAAAGGTCGAA). In this case, the GFP is expected to get targeted itself further into the nucleus after it is exported into the cytoplasm from the chloroplasts due the presence of NLS signal sequence at the N-terminal end of the target protein (GFP in this example). The SP-NLS-GFP gene cassette is into the chloroplast genome of tobacco, following the procedures essentially similar to SP-GFP construct. The subcellular localization studies show the accumulation of GFP in the nucleus.

The construct used in the study is shown in FIG. 5A. Cellular localization of SP-NLS-GFP expressed in tobacco chloroplasts is shown in FIG. 5B-D. FIGS. 5B, 5C and 5D are phase contrast, DAPI stained and GFP fluorescence viewed using confocal microscope (Nikon AIR model, respectively. The SP-NLS-GFP expressed in the chloroplasts is expected to secrete into cytoplasm due to the presence of SP and the NLS is expected to target the GFP further into the nucleus. Green fluorescence can be seen localized in the nucleus, providing direct evidence to show that the NLS from SV-40 antigen is capable of targeting the GFP into the nucleus when fused at the N-terminal end. FIGS. 5E, 5F and 5G are enlarged view of select cells, from FIGS. 5B, 5C, and 5D, respectively.

Example—6

Hygromycin Phosphotransferase as a Selectable Marker for Plastid Transformation

The present invention further tests the use of Hygromycin phosphotransferase (HPT) as a selectable marker for plastid transformation. FIG. 6 show that hygromycin can be used at 25-40 mg/l as a selection agent in tobacco plastid transformation. Transplastomic tobacco plants developed under hygromycin selection 25 mg/L are shown in FIG. 6A-D. The partial map of the construct used in the study is shown in FIG. 6E.

Advantages of the Present Invention

1. The present invention provides that the chloroplast expressed foreign proteins such as transcription factors can be targeted to the nucleus in order to regulate the nuclear genome expression.
2. The present invention provides for the export of proteins from plastids to any other organelles like mitochondria, endoplasmic reticulum and/or golgi apparatus, etc. Further chloroplast expressed foreign protein targeted to endoplasmic reticulum and/or golgi apparatus can achieve post translational modifications such as glycosylation of antibodies and other proteins that require glycosylation for their optimal function.

3. The present invention provides that certain foreign proteins expressed in chloroplasts can be phosphorylated to convert then into biologically activate form.
4. The present invention can be used to any other plant species having any plastid type.
5. The present invention can be extended to the use of nuclear selectable markers such as hygromycin phosphotransferase, PPT, kanamycin, or any other selectable marker. These markers can be used in nuclear transformation of plants including cereal crops like rice, corn, wheat, barley, etc.
6. The present invention is applicable to any organism including single cell algae (e.g. Chlamydomonas, Chorella), to higher plants like angiosperms including dicotyledons and monocotyledons.

We claim:

1. A method of expressing a foreign protein in a plastid of a host cell and secreting said protein into the cytoplasm of the host cell, comprising the steps of:
    (a) constructing a vector linked to a coding sequence of a fusion protein comprising a signal peptide sequence, wherein said signal peptide sequence is SEQ ID NO: 1, followed by in-frame fusion to a foreign gene wherein said foreign gene encodes the amino acid sequence SEQ ID NO: 3;
    (b) stably integrating said construct of step (a) into the plastid genome in the host cell; and
    (c) selecting said host cell expressing said fusion protein in the cytoplasm of said host cell.

2. The method as claimed in claim 1, wherein said amino acid sequence is encoded by a DNA sequence having SEQ ID NO:2.

3. The method as claimed in claim 1, wherein said foreign protein is encoded by a DNA sequence having SEQ ID NO:4.

4. A method of expressing a foreign protein in a plastid of a host cell, secreting said protein into the cytoplasm of the host cell, and targeting said protein to the nucleus of the host cell, comprising the steps of:
    (a) constructing a vector linked to a coding sequence of a fusion protein comprising a signal peptide sequence, wherein said signal peptide sequence is SEQ ID NO: 1, followed by in-frame fusion to a nuclear localization signal, wherein said nuclear localization signal is the amino acid sequence of SEQ ID NO: 5, followed by a foreign gene encoding a foreign protein;
    (b) stably integrating said construct of step (a) into the plastid genome; and
    (c) selecting said host cell expressing said fusion protein in the nucleus of said host cell.

5. The method as claimed in claim 4, wherein said nuclear localization signal is encoded by a DNA sequence having SEQ ID NO:6.

6. The method as claimed in claim 1, wherein said host cell is of a single cell algae.

7. The method as claimed in claim 1, wherein said host cell is from an angiosperm including monocotyledons, tobacco, and other dicotyledons.

8. The method as claimed in claim 1, wherein said host cell is a single cell algae selected from chlorella and chlamydomonas.

9. The method as claimed in claim 1, wherein said vector is incorporated into plasmid pVSR 326.

* * * * *

SEQUENCE LISTING

<160> NUMBER OF SEQ ID NOS: 6

<210> SEQ ID NO 1
<211> LENGTH: 55
<212> TYPE: PRT
<213> ORGANISM: Artificial
<220> FEATURE:
<223> OTHER INFORMATION: This protein sequence is of signal peptide of xylanase enzyme

<400> SEQUENCE: 1

Met Leu Lys Thr Leu Arg Lys Pro Phe Ile Ala Gly Leu Ala Leu Ser
1               5                   10                  15

Leu Leu Leu Thr Gly Gly Ala Ser Ser Val Phe Ala Gln Gly Asn Gly
            20                  25                  30

Gln Ala Gly Pro Pro Lys Gly Gly Ile Phe Lys Glu Gly Glu Lys Gly
        35                  40                  45

Asn Gly Asn Val Gln Pro Phe
    50                  55

<210> SEQ ID NO 2
<211> LENGTH: 165
<212> TYPE: DNA
<213> ORGANISM: Artificial
<220> FEATURE:
<223> OTHER INFORMATION: This DNA sequence encodes protein sequence of SEQ ID NO. 1

<400> SEQUENCE: 2
atgctaaaaa cgttaagaaa acccttcatt gcaggactag ctttatcatt attactcact      60
ggtggagcga gcagtgtatt tgctcaagga aacggtcaag ctggcccacc aaagggaggc     120
atttttaaag aaggagaaaa aggaaatggc aatgtccaac ctttt                     165

<210> SEQ ID NO 3
<211> LENGTH: 243
<212> TYPE: PRT
<213> ORGANISM: Artificial
<220> FEATURE:
<223> OTHER INFORMATION: This protein sequence is of Green Fluorescent Protein

<400> SEQUENCE: 3

Met Ala Ser Lys Gly Glu Glu Leu Phe Thr Gly Val Val Pro Ile Leu
1               5                   10                  15

Val Glu Leu Asp Gly Asp Val Asn Gly Tyr Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Ser Tyr Gly Val Gln Cys Phe Ser Arg Tyr Pro Asp His Met Lys
65                  70                  75                  80

```
Arg His Asp Phe Phe Lys Ser Ala Met Pro Glu Gly Tyr Val Gln Glu
             85                  90                  95

Arg Thr Ile Phe Phe Lys Asp Asp Gly Asn Tyr Lys Thr Arg Ala Glu
        100                 105                 110

Val Lys Phe Glu Gly Asp Thr Leu Val Asn Arg Ile Glu Leu Lys Gly
    115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Ala Asn Phe Lys Thr Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys His
225                 230                 235                 240

Asp Glu Leu

<210> SEQ ID NO 4
<211> LENGTH: 732
<212> TYPE: DNA
<213> ORGANISM: Artificial
<220> FEATURE:
<223> OTHER INFORMATION: This DNA sequence encodes protein sequence of
      SEQ ID NO. 3

<400> SEQUENCE: 4
atggcaagta aaggagaaga acttttcact ggagttgtcc caattcttgt tgaattagat      60
ggtgatgtta atgggtacaa attttctgtc agtggagagg gtgaaggtga tgcaacatac    120
ggaaaactta cccttaaatt tatttgcact actggaaaac tacctgttcc ttggccaaca    180
cttgtcacta ctttctctta tggtgttcaa tgcttttcaa gatacccaga tcatatgaag    240
cggcacgact tcttcaagag cgccatgcct gagggatacg tgcaggagag gaccatcttc    300
ttcaaggacg acgggaacta caagacacgt gctgaagtca agtttgaggg agacacccte    360 gtcaacagga tcgagcttaa gggaatcgat ttcaaggagg acggaaacat cctcggccac    420
aagttggaat acaactacaa ctcccacaac gtatacatca tggccgacaa gcaaaagaac    480
ggcatcaaag ccaacttcaa gacccgccac aacatcgaag acggcggcgt gcaactcgct    540
gatcattatc aacaaaatac tccaattggc gatggccctg tccttttacc agacaaccat    600
tacctgtcca cacaatctgc cctttcgaaa gatcccaacg aaaagagaga ccacatggtc    660
cttcttgagt ttgtaacagc tgctgggatt acacatggca tggatgaact atacaaacac    720
gacgaactct aa                                                        732

<210> SEQ ID NO 5
<211> LENGTH: 13
<212> TYPE: PRT
<213> ORGANISM: Artificial
<220> FEATURE:
<223> OTHER INFORMATION: This protein sequence is of nuclear
      localization signal from sv40 antigen

<400> SEQUENCE: 5
```

```
Glu Phe Leu Glu Pro Pro Lys Lys Lys Arg Lys Val Glu
1               5                   10

<210> SEQ ID NO 6
<211> LENGTH: 39
<212> TYPE: DNA
<213> ORGANISM: Artificial
<220> FEATURE:
<223> OTHER INFORMATION: This DNA sequence encodes protein sequence of
      SEQ ID NO. 5

<400> SEQUENCE: 6
gaattcctcg agcctccaaa aaagaagaga aaggtcgaa                           39
```